US00PP15087P3

(12) United States Plant Patent
Small

(10) Patent No.: US PP15,087 P2
(45) Date of Patent: Aug. 17, 2004

(54) STRAWBERRY PLANT NAMED 'CAL GIANT 5'

(50) Latin Name: *Fragaria ananassa*
Varietal Denomination: Cal Giant 5

(75) Inventor: David W. Small, Arroyo Grande, CA (US)

(73) Assignee: California Giant, Inc., Watsonville, CA (US)

( * ) Notice: Subject to any disclaimer, the term of this patent is extended or adjusted under 35 U.S.C. 154(b) by 10 days.

(21) Appl. No.: 10/274,216

(22) Filed: Oct. 17, 2002

(65) Prior Publication Data

US 2004/0078856 P1 Apr. 22, 2004

(51) Int. Cl.[7] ..... A01H 5/00

(52) U.S. Cl. ..... Plt./209

(58) Field of Search ..... Plt./209

*Primary Examiner*—Bruce R. Campell
*Assistant Examiner*—Michelle Kizilkaya
(74) *Attorney, Agent, or Firm*—David A. Farah; Sheldon & Mak

(57) ABSTRACT

A new and distinct variety of strawberry plant named 'Cal Giant 5' that is a short-day style of plant with a strong ever-bearing tendency, producing runners freely at the nursery while producing high levels of fruit early in the fruiting season, and continuing production through the summer and into the autumn months. 'Cal Giant 5' displays very good tolerance to a number of soil-borne, foliar and fruit diseases, and pollinates exceptionally well in both inclement and ideal conditions, retaining size, shape, high gloss, and overall good appearance throughout the entire season.

5 Drawing Sheets

Latin name of the genus and species of the plant claimed: The Latin name of the plant is *Fragaria ananassa.*

BACKGROUND OF THE INVENTION

This new variety of strawberry, named 'Cal Giant 5,' resulted from a cross performed in 1997 between two proprietary plant varieties, which the grower believes to have been the proprietary plant variety designated 'F39.1' and the proprietary plant variety designated 'F15.1.' However, the records showing the parentage of 'Cal Giant 5' were destroyed in a fire on Jun. 8, 2001 at the office of the grower and the parentage of 'Cal Giant 5' is, therefore, not certain. Assuming that the parentage was the proprietary plant variety designated 'F39.1' and the proprietary plant variety designated 'F15.1,' both proprietary plant varieties were maintained exclusively for breeding purposes during the year 1997, have not been maintained after 1997, have not been released to growers, and have not been the subject of an application for a plant patent in the United States.

'Cal Giant 5' was first selected as a seedling variety at the California Giant, Inc. Santa Maria, Calif. breeding test plot in 1999 and has been propagated asexually by runners at Malin, Oreg., U.S. (42° N., 121.4° W.). It was originally designated '65H1,' and later designated 'H1.' Asexual propagules from this original source have been placed in test plots in the fruiting areas of Oxnard, Santa Maria, and Watsonville, Calif., U.S. This propagation and testing have demonstrated that the combination of traits disclosed herein which characterize propagules of 'Cal Giant 5' are fixed and retained true to type through successive generations of asexual reproduction.

SUMMARY OF THE INVENTION

'Cal Giant 5' is a new and distinct strawberry variety characteristically different from any other strawberry variety known to the inventor. 'Cal Giant 5' is a short-day style of plant with a strong ever-bearing tendency; running freely at the nursery, producing a very high yielding early season crop, and continuing production through the summer and into the autumn months. Among the characteristics that distinguish 'Cal Giant 5' are a combination of traits that include high levels of production in each of the three main production areas in California (Oxnard, Santa Maria, and Watsonville, Calif.), exceptional flesh firmness, exceptional skin firmness, good flavor, retention of fruit size, and the combination of exceptional high early fruit yield in concert with a strong ever-bearing tendency. In addition 'Cal Giant 5' produces well on a strong and vigorous plant in both fumigated and non-fumigated conditions. Fruit from 'Cal Giant 5' pollinates exceptionally well in inclement weather, with little incidence of fruit rot, allowing for continued production of well shaped, marketable fruit following cold, moist conditions.

BRIEF DESCRIPTION OF THE FIGURES

The accompanying color photograph show typical specimens of the new strawberry variety designated 'Cal Giant 4,' including fruit, foliage, and flower, at the age of about eight months, as nearly true as it is possible to make in color reproductions.

DETAILED BOTANICAL DESCRIPTION OF THE NEW VARIETY

The following is a detailed description of 'Cal Giant 5' in accordance with UPOV terminology. Unless otherwise noted, this detailed description is based on observations taken during the 2002 growing season in Oxnard, Santa Maria, and Watsonville, Calif., U.S.

Color terminology used herein is in accordance with the Pantone® Color Formula Guide 1000 and the Pantone® Formula Guide, as given below (Pantone Inc., 590 Commerce Boulevard, Carlstadt, N.J. U.S. 07072-3098). The color description and color illustrations are as nearly true as is reasonably possible. However, it is understood that both color and phenotypic expressions described herein may vary from plant to plant with differences in growth, environment and cultural conditions, without any change in the genotype of the variety 'Cal Giant 5.'

Unless specified otherwise, the 'Cal Giant 5' plants described and depicted in this disclosure are eight months old.

Botanical Classification and Parentage:

'Cal Giant 5' is a member of the genus Fragaria and species *ananassa*. As discussed above, it is believed to be a cross between the proprietary plant variety designated 'F39.1' and the proprietary plant variety designated 'F15.1.' 'Cal Giant 5' is distinguished from its parents in that 'Cal Giant 5' has a stronger tolerance to soil-borne diseases, has a more contained plant architecture, with a greater propensity toward early fruit production than either of its parents. Additionally, the fruit of 'Cal Giant 5' has greater flesh firmness, greater skin firmness, better interior color, and greater retention of fruit size between primary and tertiary fruit within the individual inflorescence than either of its parents.

Figure 1:
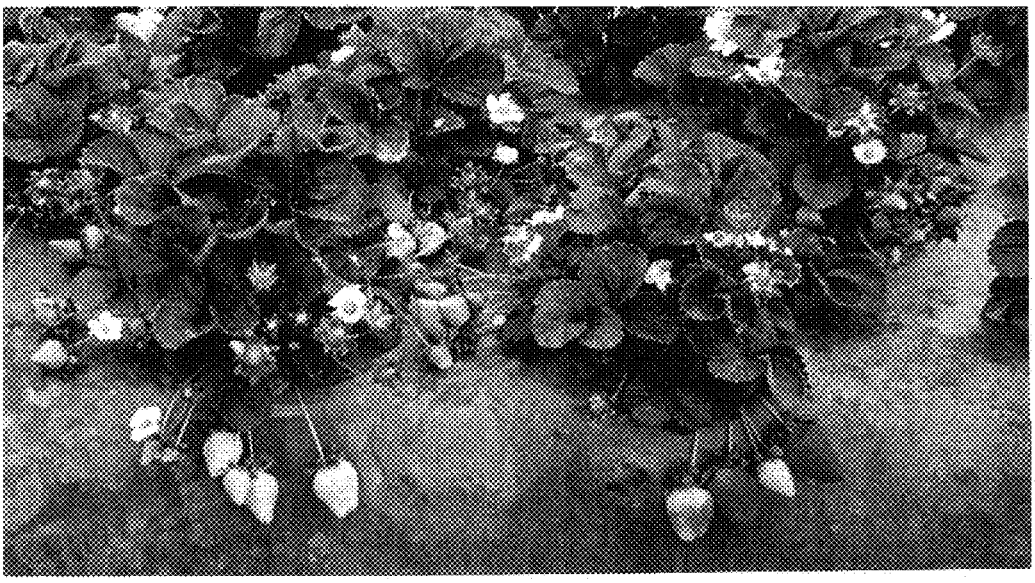
FIG. 1 is a color photograph taken in Santa Maria, Calif. during April 2002 showing the typical early season plant architecture, typical early season fruiting habit, typical early season fruit shape, and continuing early season fruit size of 'Cal Giant 5;'
Figure 2:
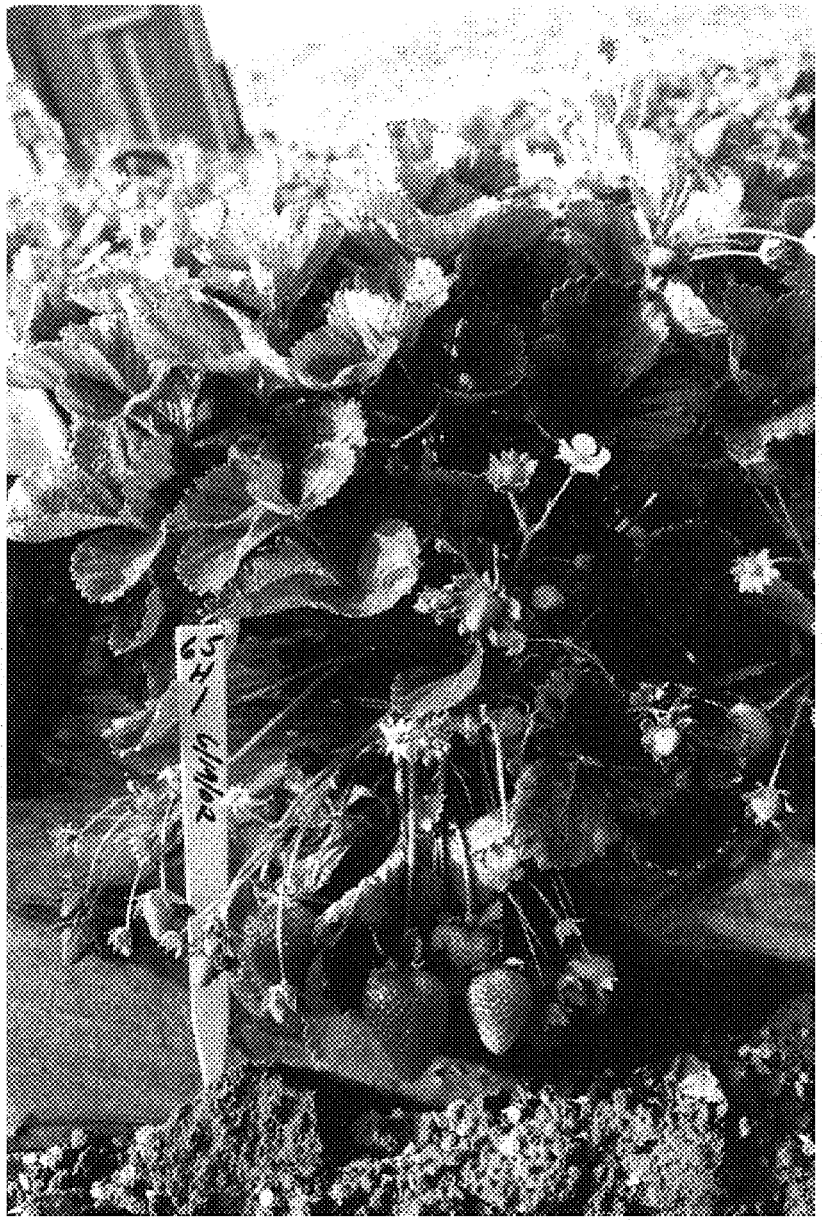
FIG. 2 is a color photograph taken in Watsonville, Calif. on Jun. 19, 2002 showing the typical late season plant architecture, typical late season fruiting habit, typical late season fruit shape, and continuing late season fruit size of 'Cal Giant 5;'

Physical Description:

Referring now to FIG. 1 and FIG. 2, there are shown color photographs taken during April 2002, and on Jun. 19, 2002, showing the general plant architecture, flowering and fruiting characteristics of plants of 'Cal Giant 5' grown in a standard, fumigated, cultural system. As can be seen further in FIG. 1 and FIG. 2, the plant architecture is typically semi-erect and semi-open.

As disclosed in this disclosure, the descriptions of general leaf morphology relate to all leaves within the plant, and the leaf measurements relate to mid-tier leaves within the plant. 'Cal Giant 5' leaves are stipulate, petiolate, have pinnate veination, and are mildly conduplicate. Further, 'Cal Giant 5' leaves exhibit winged, paired stipules at the base of the stem. Stipule length ranges from 33 mm to 43 mm, with an average length of 38 mm. Leaflets are trifoliate and are generally slightly ovate and rarely oblong in shape. The leaf base tends to be obtuse and shortly attenuate. The leaf apice is rounded. The leaf margin is crenate, bearing an average of 19 serrations per leaflet. The cuticle tends to be dull to lightly waxy in appearance. Leaf thickness is approximately 0.5 mm. Leaflet diameter ranges between 72 mm and 100 mm, averaging 90.4 mm. Leaflet length ranges from 82 mm to 100 mm, averaging 91.9 mm.

'Cal Giant 5' leaves tend to be dark green in color, darker green than 'Cal Giant 2' (U.S. Plant Pat. No. 12,221) and 'Cal Giant 3' (U.S. Plant Pat. No. 12,403) but not as dark green as 'Cal Giant 4' (U.S. Plant Pat. No. 12,423). Visual comparisons of 'Cal Giant 5' leaf color to 'Cal Giant 2,' 'Cal Giant 3,' and 'Cal Giant 4' were made using the Pantone® Color Formula Guide 1000 and the Pantone® Formula Guide and the results are given in Table 1.

TABLE I

Visual Comparison of 'Cal Giant 5' Leaf and Fruit Color to 'Cal Giant 2,' 'Cal Giant 3,' and 'Cal Giant 4'

| | Adaxial Leaf | Abaxial Leaf | External Fruit | Interior Fruit |
|---|---|---|---|---|
| 'Cal Giant 5' | 5747C | 5763C | 179C | 172C |
| 'Cal Giant 2' | 363U | 370U | Warm Red | Warm Red |
| 'Cal Giant 3' | 364U | 371U | 1788 U2X | 1788 U2X |
| 'Cal Giant 4' | 576U | 577U | 1797U | 186C |

Figure 3:
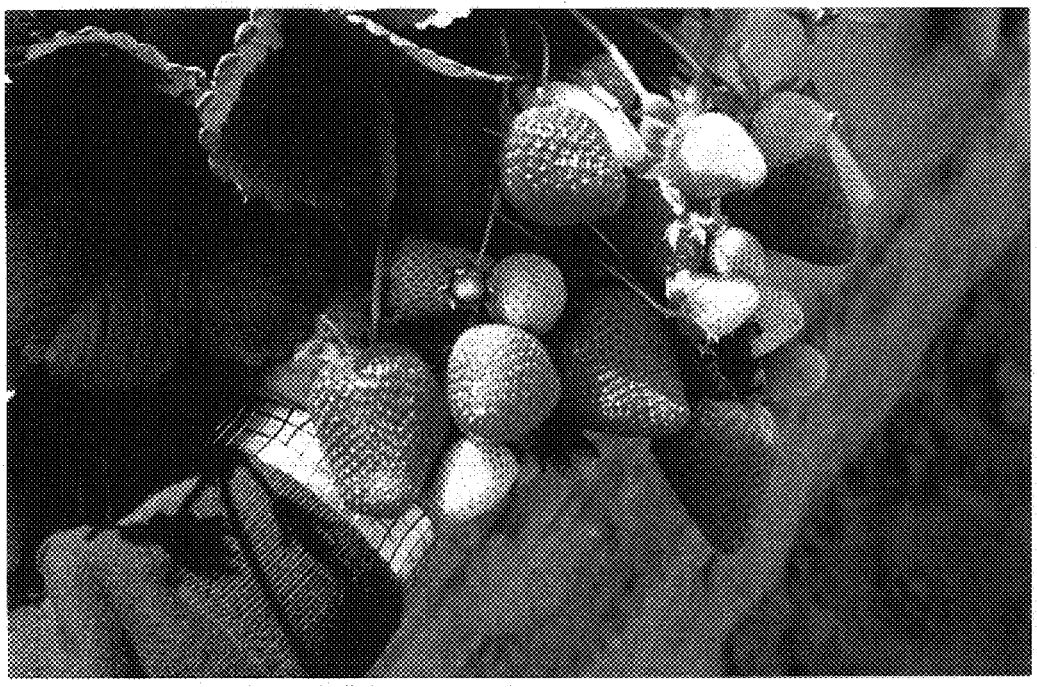
FIG. 3 is a color photograph taken in Watsonville, Calif. during the month of May 2002 showing typical mid-season fruit appearance; including shape, color, and size (as well as uniformity of size within the inflorescence)

Referring now to FIG. 3, there is shown a color photograph taken in Watsonville, Calif. during the month of May 2002 showing typical mid-season fruit appearance; including shape, color, and size (as well as uniformity of size within the inflorescence). As can be seen, blooms and fruit of 'Cal Giant 5' develop well away from the plant, advantageously easing harvest and allowing for good ventilation, reducing the incidence of fruit diseases. The fruit are borne on a dichasium cyme. Inflorescence length ranges from 29 cm to 35.2 cm, averaging 32.22 cm, essentially the same as 'Cal Giant 3' (32.85 cm), slightly longer than 'Cal Giant 2' (30.9 cm), and shorter than 'Cal Giant 4' (35.64 cm). Peduncle length to the point of pedicel connection ranges from 3 cm to 15.5 cm and average 9.9 cm. Peduncle diameter ranges from 4 mm to 6 mm and average 5 mm. Pedicel develop from the peduncle inside the crown, early in the fruiting season, with single pedicels arising from the crown. As the growth season progresses, the development of the pedicel from the peduncle occurs above the crown.

The peduncle and pedicel of 'Cal Giant 5' are smooth and finely pubescent with pubescence measuring 1 mm in length and standing at a 90° angle to the peduncle and pedicel. Bract leaves are present and either alternate or appear opposite each other at the base and along the pedicel. Petiole length ranges from 16.6 cm to 31 cm, and average 24.5 cm in length. Mid-point petiole diameter ranges from 3 mm to 4.5 mm, averaging 3.7 mm. Petioles are smooth, sparsely pubescent with pubescence measuring 1 mm in length and standing at a 90° angle to the petiole.

Corolla diameter ranges from 26 mm to 36 mm, averaging 32.1 mm. There are five overlapping white petals per corolla. Additionally, a gap forms between two of the five petals on each corolla averaging about 1 mm in width. Petal diameter ranges from 13 mm to 20 mm, averaging 16.4 mm.

Calyces are pubescent and are not inserted into the shoulder. Sepals overlap, and, in an alternating pattern, every other sepal reflexes, while the neighboring sepal clasps. Calyces of 'Cal Giant 5' are smooth. Calyces are the same color as the adaxial leaf surface. Calyx diameter ranges from 39 mm to 62 mm, averaging 50.8 mm.

Stamen are arranged irregularly in three tiers. The number of stamen per bloom range from 22 to 26, averaging 25.6. Filament length varies from 0.5 mm to 4 mm.

Figure 4:
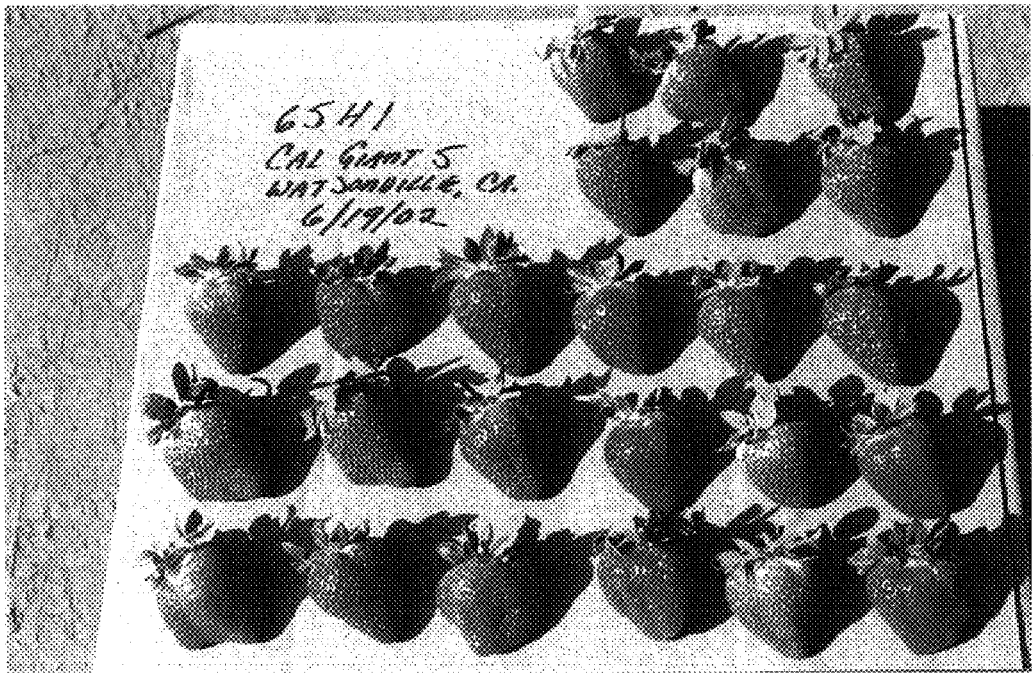
FIG. 4 is a color photograph taken in Watsonville, Calif. on Jun. 19, 2002 showing typical fruit shape and exterior color of the fruit of 'Cal Giant 5.
Figure 5:
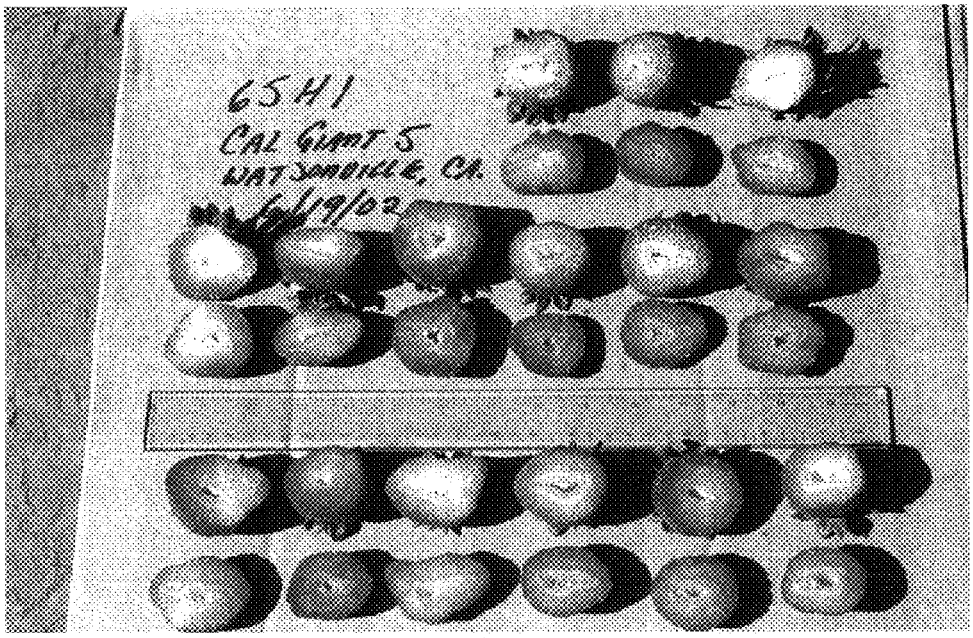
' and FIG. 5 is a color photograph taken in Watsonville, Calif. on Jun. 19, 2002 showing typical fruit structure and interior fruit color of the fruit of 'Cal Giant 5.'

FIG. 4 is a color photograph taken in Watsonville, Calif. on Jun. 19, 2002 showing typical fruit shape and exterior color of the fruit of 'Cal Giant 5.' As can be seen, fruit shape varies between conic and wedge shaped with a slightly rugose to smooth surface. There is no difference in fruit shape and skin texture between primary, secondary and tertiary fruit. Primary fruit tends to be 20% larger than secondary fruit and 40% larger than tertiary fruit. 'Cal Giant 5' fruit size remains very good throughout the season. Commercially harvested, first quality fruit average 28.79 grams per berry. Commercial yields of first quality fruit average 1,000 grams per plant. The fruit of 'Cal Giant 5' has an exceptional gloss. Seeds are positioned even with the surface of the fruit and vary in color from yellow to red, depending upon level of ripeness. The color of the fruit of 'Cal Giant 5' is darker than the color of the fruit of 'Cal Giant 2', similar in color to the fruit of 'Cal Giant 3' and lighter than the color of the fruit of 'Cal Giant 4.' A comparison of exterior and interior fruit color, utilizing the Pantone® Color Formula Guide 1000 and the Pantone® Formula Guide are included in Table I.

The ratio of the width of the conic fruit to the length of the conic fruit is 5.7:4.3 (0.75). The ratio of the width of the wedge shaped fruit to the length of the wedge shaped fruit is 5.2:4.6 (0.88).

Flesh and skin firmness of 'Cal Giant 5' are exceptional, significantly firmer than 'Cal Giant 2,' 'Cal Giant 3,' and 'Cal Giant 4.' The soluble solid content of 'Cal Giant 5' fruit was determined (8.0%) utilizing a Westover® Model RHB-32ATC Hand Held Brix Refractometer. Flavor of the 'Cal Giant 5' is not as consistently sweet as 'Cal Giant 3,' sweeter than 'Cal Giant 4' and has a more balanced flavor than 'Cal Giant 2.'

Protein Characteristics:

The isoenzyme banding pattern of 'Cal Giant 5' as determined by gel electrophoresis is compared with 'Cal Giant 2,' 'Cal Giant 3,' and 'Cal Giant 4' in Table II, below.

TABLE II

Comparisons of 'Cal Giant 5' Isoenzyme Banding Patterns with the Isoenzyme Banding Patterns of 'Cal Giant 2,' 'Cal Giant 3,' and 'Cal Giant 4'

| | Phosphoglucoseisomerase (PG1) | Leucine Aminopeptidase (LAP) | Phosphoglucomutase (PGM) |
|---|---|---|---|
| 'Cal Giant 5' | A1 | B3 | C2 |
| 'Cal Giant 2' | A2 | B3 | C2 |
| 'Cal Giant 3' | A3 | B3 | C2 |
| 'Cal Giant 4' | A2 | B3 | C4 |

Resistance to Diseases and Pests:

'Cal Giant 5' remains extremely healthy and produces an exceptional crop in both fumigated and non-fumigated soil. 'Cal Giant 5' displays tolerance to *Verticillium wilt,* Phytophthora spp. *Rhizoctonia fragariae,* and Pythium spp. Further, 'Cal Giant 5' displays good tolerance to powdery mildew (*Sphaerotheca macularis*), common leaf spot (*Mycosphaerella fragariae*), grey mold (*Botrytis cinerea*), and Collectotrichum spp. 'Cal Giant 5' also displays resistance to Tetranychus sp.

Productivity Characteristics:

'Cal Giant 5' produces a very strong early season crop and continues production through the summer and into the autumn months. Though the 'Cal Giant 5' runs freely at the nursery, it produces very few, if any, runners in the fruit production fields. 'Cal Giant 5' produces well in each of the three primary strawberry fruiting districts of California.

'Cal Giant 5' pollinates exceptionally well in inclement weather and displays exceptional tolerance to rainy conditions with little breakdown of skin due to saturation and little incidence of rot due to rain. These characteristics allow for continued early season production in all of the three major production areas of California. In the southern California production region 'Cal Giant 5' has the potential to produce 75% of its fresh market production within a 5-week period; as well as continuing on to produce a significant yield during the processing fruit harvest period. The 'Cal Giant 5' produces a significantly high percentage of highly flavorful, well-formed, exceptionally firm, well-sized fruit, insuring that the majority of the fruit manufactured by the plant will be marketable with unusually low cull rates. 'Cal Giant 5' also produces a high yield of very acceptable processing fruit with good firmness, high soluble solids, good exterior color, good interior color, and ease of capping.

What is claimed:

1. A new and distinct strawberry plant designated 'Cal Giant 5' as herein described and illustrated.

* * * * *